United States Patent [19]

Fu

[11] 4,388,229

[45] Jun. 14, 1983

[54] CONTACT LENS REJUVENATING SOLUTION

[75] Inventor: Cherng-Chyi Fu, Sunnyvale, Calif.

[73] Assignee: Syntex (U.S.A.) Inc., Palo Alto, Calif.

[21] Appl. No.: 317,656

[22] Filed: Nov. 2, 1981

[51] Int. Cl.$^3$ .......................... C11D 1/72; C11D 7/48
[52] U.S. Cl. .................... 252/549; 252/89.1;
    252/173; 252/174.21; 252/174.23; 252/179;
    252/547; 252/DIG. 2; 252/DIG. 14
[58] Field of Search ................. 252/89.1, 173, 174.21,
    252/174.23, 174.25, 179, 549, 547, 558, 559,
    DIG. 2, DIG. 14; 210/679, 683; 521/28, 32, 38;
    424/79

[56] References Cited

U.S. PATENT DOCUMENTS

| | | | |
|---|---|---|---|
| 2,684,321 | 7/1954 | Thurmon et al. | 424/79 |
| 2,855,371 | 10/1958 | Abrams | 521/28 |
| 3,024,207 | 3/1962 | Shaw et al. | 260/2.1 |
| 3,171,752 | 3/1965 | Rankin | 106/194 |
| 3,888,782 | 6/1975 | Boghosian et al. | 252/106 |
| 3,954,644 | 5/1976 | Krezanoski et al. | 252/106 |
| 4,152,283 | 5/1979 | Cordrey et al. | 252/99 |
| 4,200,695 | 4/1980 | Chong et al. | 521/28 |
| 4,280,920 | 7/1981 | Garvey et al. | 252/173 |
| 4,347,328 | 8/1982 | Harmon et al. | 521/28 |

*Primary Examiner*—P. E. Willis, Jr.
*Attorney, Agent, or Firm*—Howard M. Peters; Joseph I. Hirsch

[57] ABSTRACT

A solution for removing occluded and adsorbed chemicals, such as cationic preservating agents, anionic preserving agents and mixtures thereof, from contact lenses which comprises a nonionic surfactant; a cationic ion exchange resin, an anionic ion exchange resin, or mixtures thereof; water; and optionally sodium chloride. Such solutions are useful to reduce and prevent irritation of the eye of the contact lens wearer.

41 Claims, No Drawings

CONTACT LENS REJUVENATING SOLUTION

BACKGROUND OF THE INVENTION

1. Field of the Invention

This invention relates generally to solutions for removing occluded and adsorbed chemicals, such as cationic preserving agents, anionic preserving agents or mixtures thereof, from contact lenses which comprises a nonionic surfactant; a cationic ion exchange resin, an anionic ion exchange resin, or mixtures thereof; water; and optionally sodium chloride. Such solutions are useful to reduce and prevent chemical irritation of the eye of the contact lens wearer.

2. Related Disclosures

The widespread development of the contact lens technology and contact lens use did not occur until the expansion of polymer and plastic chemistry in the 1930's and 1940's. It is useful to classify contact lenses as being hard, rigid, gas-permeable, flexible, or soft hydrogel, depending upon the structural characteristics of the material used to fabricate the lens. The majority of the lenses in use today are made of, or include some, poly(-methylmethacrylate). Polymers and copolymers of polymethylmethacrylate, cellulose acetate butyrate, siloxanes, fluoroalkyl-methylmethacrylate, N-vinyl-2-pyrrolidone and the like may be classified as hard or flexible, depending upon the ratio of the components. Silicone rubber and silicone-polycarbonate polymers are usually classified as flexible polymers. Soft contact lenses are usually made from cross-linked hydrophilic polymers and copolymers such as 2-hydroxyethylmethacrylate 2,3-dihydroxypropylmethacrylate, methyl methacrylate, methacrylic acid, N-vinyl-2-pyrrolidone, and the like which can be hydrated with about 20-85 percent water. A recent review by M. Refojo on current contact lens technology can be found in the *Encyclopedia of Chemical Technology*, Kirk-Othmer, Ed., Vol. 6, 3rd ed., published in 1979 by John Wiley and Sons, pp. 720-742.

Soft contact lenses of the hydrated gel type have a number of properties which pose problems for the wearer. One of these problems is the method of cleaning and sterilizing the lenses. One sterilization method (the hot method) is to boil the lenses in water or saline solution. Other methods of cleaning and sterilization (chemical methods) include treating the lenses with a 3% solution of hydrogen peroxide followed by rinsing with a solution containing a neutralizing agent and preserving composition. Compounds which have been useful in contact lens solutions as bactericides and germicides or preserving agents include chlorhexidene digluconate, alkyltriethanol ammonium chloride, iodophors, thimerosal (a mercury compound), chlorobutanol, benzalkonium chloride, sodium tetracemedine sorbic acid, phenylmercuric chloride and cetyl pyridinium chloride. It is known that many of these preservatives concentrate with time in the hydrogel soft contact lenses. When these concentrated preservatives are subsequently released to the cornea during wearing, they may cause serious chemical burns. Other wearers have experienced allergic responses to these chemicals, even at low concentrations.

Nearly all of the contact lens solutions presently being marketed use chlorhexidene, thimerosal, or benzalkonium chloride as preservative agents. Some solutions such as SOFTMATE, marketed by Barnes-Hind, Inc.; FLEXCARE and DISINFECTING SOL'N marketed by Bausch and Lomb; and FLEXSOL marketed by Burton Parsons Co. Inc., use a mixture of chlorhexidine and thimerosal as the preserving agent.

Chlorhexidine, a type of biguanide compound which is a popular component of current contact lens solutions, has the chemical name, 1,1'-hexamethylene-bis-[5-(p-chlorophenyl)]biguanide and the following chemical structure:

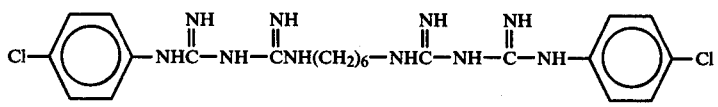

Chlorhexidine is sold under trademarks such as HIBITANE, NOLVAEAN, ROTUSEPT and STERILON. Their use in contact lens solutions is detailed in U.S. Pat. Nos. 3,882,036 and 3,888,782, which are incorporated herein by reference. Several derivatives such as the diacetate and digluconate (also known as HIBISCRUB) are also available.

Thimersal, a type of anionic organic mercury compound, is a current preservative of contact lens solutions with the chemical name, sodium ethylmercurithiosalicylate, and has the following structure:

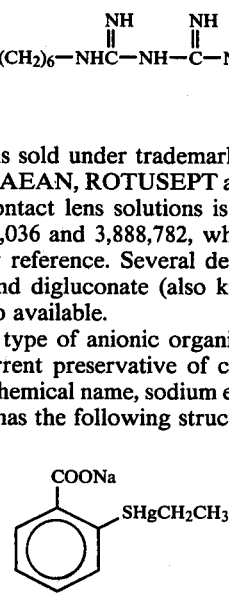

Thimerosal is also sold under trademarks such as MERTHIOLATE SODIUM, MERZONIN, MERTORGAN, and MERFAMIN. Its use in contact lens solutions is discussed in U.S. Pat. Nos. 3,888,782 and 4,029,817, which are incorporated herein by reference.

Benzalkonium chloride, a mixture of alkyl dimethylbenzylammonium chlorides, is also currently used as a preservative, and has the following generalized structure:

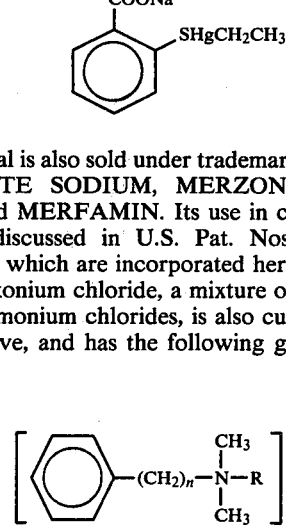

where R represents a mixture of alkyls from $C_8H_{17}$ to $C_{18}H_{37}$, and n is an integer from 1-5.

Benzalkonium chloride is also sold under trademarks such as ZEPHIRAN CHLORIDE, ZEPHIROL, BTC, ROCCAL, BENIROL, ENUCLEN, GERMITEL, DRAPOLENE, DRAPOLEX, CEQUARTYL, PARALKAV, GERMINOL, RODALON and OSVAN. Its use in contact lens solution is discussed in U.S. Pat. No. 3,882,036 which is incorporated herein by reference.

It is an object of this invention to provide chemical solutions to rejuvenate a hard, rigid, gas-permeable or soft contact lens, particularly a soft hydrogel lens, by removal of most or essentially all of the chemical agents, such as bactericides, preservatives and germicides adsorbed by the lens during sterilization and cleaning.

It is a further object of this invention to provide a process for rejuvenating hard, rigid, gas permeable, or soft hydrogel contact lenses.

It is a further object of this invention to provide a process for preparing compositions useful for rejuvenating hard, rigid, gas-permeable or soft hydrogel contact lenses.

SUMMARY OF THE INVENTION

One aspect of this invention is an aqueous contact lens solution for removing adsorbed and occluded chemical and biological agents from a contact lens in need of rejuvenation which comprises:
(a) a nonionic surfactant;
(b) (i) a cationic ion exchange resin,
 (ii) an anionic ion exchange resin, or
 (iii) mixtures of (i) and (ii);
(c) water; and optionally
(d) an ophthalmologically suitable salt.

Another aspect of the invention is a method of rejuvenating contact lenses by contacting said lens with the solutions disclosed herein.

Another aspect of this invention is preparing the rejuvenating solutions disclosed herein.

DETAILED DESCRIPTION OF THE INVENTION

The broad aspect of this invention relates to a composition for rejuvenating contact lenses, i.e., removal of adsorbed and occluded chemical agents which have been previously used in the sterilization and cleaning of the lens. The composition is also useful to remove any medications used in treatment of the eye which are subsequently adsorbed by the lens. More specifically, the composition is composed of surfactants made up of polyoxygenated long-chain carboxylic acid esters of sorbitol, sorbitan or sorbide in combination with a cationic ion exchange resin and a saline solution. These compositions are particularly useful to remove alkyl or aryl quaternary amines and their salts from hard or soft hydrogel lenses.

Another aspect of the invention is a composition composed of surfactants made up of polyoxygenated long chain carboxylic acid esters of sorbitol, sorbitan or sorbide in combination with an anionic ion exchange resin and a saline solution. These compositions are useful to remove anionic chemicals (preservatives, bactericides, etc.) from hard, rigid, gas permeable or soft hydrogel lenses.

Another aspect of this invention is a composition composed of surfactants made up of polyoxygenated long-chain carboxylic acid esters or sorbitol, sorbitan or sorbide in combination with a mixture of cationic and anionic ion exchange resins as described above and a saline solution. These compositions may be used to remove both cationic and anionic chemicals from hard rigid, gas permeable or soft hydrogel contact lenses.

The Composition

The rejuvenating properties of the aqueous solutions of this invention are achieved by the use of the combination of:
(a) a nonionic surfactant;
(b) (i) a cationic ion exchange resin,
 (ii) an anionic ion exchange resin, or
 (iii) mixtures of (i) and (ii);
(c) water, and optionally,
(d) an ophthalmologically suitable salt;
in amounts effective to remove the offending chemical agents and reduce the irritating effect on the eye.

Solutions contemplated hereby include not only true solutions wherein all solutes have dissolved completely, but also describe compositions wherein some components may be suspended or insoluble in the composition.

Surfactants

A surface-active agent (a surfactant) is a substance that when present in fairly low concentrations in a system has the property of adsorbing onto the surfaces or interfaces of the system and of altering to a marked degree the surface or interfacial free energies of those surfaces (or interfaces). The term "interface" herein indicates a boundary between any two immersible phases. A more complete description of the concepts of surface active agents is found in *Surfactants and Interfacial Phenomena* by Milton J. Rosen, published by John Wiley and Sons of New York in 1978.

Stated in another manner, surface active agents have a characteristic molecular structure (amphipathic) consisting of a group that has little attraction for the solvent (lypophobic or hydrophilic group) and a group that has a strong attraction for the solvent (lypophilic or hydrophobic group). The hydrophobic group is usually a long-chain hydrocarbon residue and the hydrophilic group is an ionic or highly polar group. Depending on the nature of the hydrophilic group, surfactants are classified as anionic (negative), cationic (positive), zwitterionic (containing both positive and negative charges) and nonionic.

Any nonionic surfactant which is ophthalmologically acceptable may be useful in the present invention. The following list of nonionic surfactants is only representative of the classes known in the art:

SURFACTANTS

Esters of long-chain carboxylic acids
Long-chain carboxylic acid esters of glycerol and polyglycerol and their derivatives
Long-chain carboxylic acid esters of polyoxyethylenated glucose and polyoxyethylenated glucosides
Long-chain carboxylic acid esters of polyoxyethylenated sorbitol, sorbitan, or sorbide
Long-chain carboxylic acid esters of (poly)oxyethylene glycols; (poly)oxyethylenated fatty acids
Long-chain carboxylic acid esters of (poly)oxypropylene glycols; (poly)oxypropylenated fatty acids
Polyoxyethylenated long-chain carboxylic acid esters of polyoxypropylene glycols; polyoxyethylenated polyoxypropylenated fatty acids
Long-chain carboxylic acid esters of other polyhydric alcohols
Ethers of (poly)oxyethylene glycols
Alkylnaphthyl ethers of (poly)oxyethylene glycols and their ethers
Alkylnaphthyl ethers of (poly)oxyethylene glycols and their ethers; (poly)oxyethylenated alkylphenols and their ethers
Alkyl and cycloalkyl esters of (poly)oxyethylene glycols and their ethers; (poly)oxyethylenated alcohols and their ethers or short-chain esters Polyoxyethylenated polyoxypropylene glycols and their ethers
Tertiary acetylenic glycols
Thio ethers of (poly)oxyethylene glycols (poly)oxyethylenated mercaptans
Amides of long-chain carboxylic acids
Acylated primary and secondary alkanolamines
Fatty acid-secondary N-($\beta$-hydroxyethyl)amine "condensates;" diethanolamides
N-(Poly)oxyethylenated amides with 16 moles of ethylene oxide
Polyoxyethylenated amides with 15 moles of ethylene oxide
Mono-and di-isopropanolamides Presently prefered surfactants of this invention include polyoxyethylenated long-chain carboxylic acid polyesters of sorbitol, sorbitan and sorbide and mixtures thereof. Sorbitol is also known as D-sorbite, D-sorbitol, and hexahydric alcohol (usually 1,2,3,4,5,6-hexanhexol). Sorbitan is also known as monoanhydrosorbitol and sorbitol anhydride, and is a generic name for anhydrides derivable from sorbitol by the removal of one molecule of water. Sorbide is also known as dianhydrosorbitol, and is the generic name for anhydrides derived from sorbitol by removal of two molecules of water.

Representative surfactants are produced and marketed under trademarks such as TWEEN, (G- No. and ATLOX) BRIJ (Atlas Chemical Co.), DREWMULSE (Drew Chemical Corp.) and SYLVAN (Sylvan Chemical Co.). They include:

| SURFACTANTS | |
|---|---|
| TRADEMARK | NOMINAL CHEMICAL STRUCTURE (EO is ethylene oxide) |
| TWEEN 20 | Polyoxyethylenated sorbitan monolaurate (20 moles EO) |
| DREWMULSE POE—SML | Polyoxyethylenated sorbitan monolaurate (20 moles EO) |
| TWEEN 21 | Polyoxyethylenated sorbitan monolaurate |
| SYLVAN POLY SL-96 | Polyoxyethylenated sorbitan monolaurate (4 moles EO) |
| G-1045 | Polyoxyethylenated sorbitol laurate |
| TWEEN 40 | Polyoxyethylenated sorbitan monopalmitate (20 moles EO) |
| DREWMULSE POE—SMP | Polyoxyethylenated sorbitan monopalmitate (20 moles EO) |
| TWEEN 60 | Polyoxyethylenated sorbitan monostearate (20 moles EO) |
| DREWMULSE POE—SMS | Polyoxyethylenated sorbitan monostearate (20 moles EO) |
| TWEEN 61 | Polyoxyethylenated sorbitan monostearate (4 moles EO) |
| TWEEN 65 | Polyoxyethylenated sorbitan tristearate (20 moles EO) |
| DREWMULSE POE—STS | Polyoxyethylenated sorbitan tristearate (20 moles EO) |
| TWEEN 80 | Polyoxyethylenated sorbitan monooleate (20 moles EO) |
| TWEEN 81 | Polyoxyethylenated sorbitan monooleate (5 moles EO) |
| TWEEN 85 | Polyoxyethylenated sorbitan trioleate (20 moles EO) |
| G-1086 | Polyoxyethylenated sorbitol hexaoleate |
| G- (or ATLOX) 1096 | Polyoxyethylenated sorbitol hexaoleate |
| ATLOX 1087 | Polyoxyethylenated sorbitol septaoleate |
| ATLOX 1045-A | Polyoxyethylenated sorbitol oleate-laurate |
| ATLOX 1256 | Polyoxyethylenated sorbitol-tall-oil ester |
| ATLOX 1255 | Polyoxyethylenated sorbitol-tall-oil ester |
| G-1234 | Polyoxyethylenated sorbitol-tall-oil ester |
| G-1702 | Polyoxyethylenated sorbitol-beeswax ester |
| G-1726 | Polyoxyethylenated sorbitol-beeswax ester |
| G-1441 and G-1471 | Polyoxyethylenated sorbitol-lanolin esters |

An additional source of suitable surfactants useful in this invention is the Atlas Chemical Corp., which produces a line of BRIJ ® emulsifiers. Representative members of this series include:

| SURFACTANTS | |
|---|---|
| TRADEMARK | NOMINAL CHEMICAL STRUCTURE |
| BRIJ 30 | Polyoxyethylene 4 lauryl ether |
| BRIJ 35 | Polyoxyethylene 23 lauryl ether |
| BRIJ 52 | Polyoxyethylene 2 cetyl ether |
| BRIJ 56 | Polyoxyethylene 10 cetyl ether |
| BRIJ 58 | Polyoxyethylene 20 cetyl ether |
| BRIJ 72 | Polyoxyethylene 2 stearyl ether |
| BRIJ 76 | Polyoxyethylene 10 stearyl ether |
| BRIJ 78 | Polyoxyethylene 20 stearyl ether |
| BRIJ 93 | Polyoxyethylene 2 oleyl ether |
| BRIJ 97 | Polyoxyethylene 10 oleyl ether |
| BRIJ 99 | Polyoxyethylene 20 oleyl ether |

The presently preferred surfactants for use in this invention are those produced by the Atlas Chemical Co., including TWEEN 20, 21, 40, 60, 61, 65, 80, 81, 85 and various mixtures thereof. A presently most preferred surfactant is TWEEN 20.

These surfactants and mixtures thereof may be present in quantities in the range of about 0.1 to 10 percent by weight of the liquid component, preferably about 0.5 to 5 percent by weight. Most preferably, the surfactant is present in about 1 to 3 percent by weight of the final solution. Mixtures of surfactants are also useful in this invention.

Ion-Exchange Resins

Cationic ion exchange resins are produced by a number of companies, including Bio-Rad, Dow Chemical (Dow), Diamond Shamrock (Diamond), Rohm and Haas (Rohm) and Permutit Co. (Perm). Cationic ion exchange resins may be strongly acidic such as the phenolics (sulfonic acids) which are sold under the following trademarks: BIO-REX 40 (Bio-Rad), DOWEX (Dow), C-3 (Diamond), and ZEOCARB 215 (Perm.). Other strongly acidic cation exchange resins include the polystyrene based sulfonic acids which are sold under the following trademarks:

| CATION ION-EXCHANGE RESINS | | |
|---|---|---|
| Bio-Rad | Dow (DOWEX) | Rohm and Haas (AMBERLITE) |
| AG 50W-X1 | 50W-X1 | |
| AG 50W-X2 | 50W-X2 | IR-116 |
| AG 50W-X4 | 50W-X4 | IR-118 |
| AG 50W-X8 | 50W-X8 | IR-120 |

| CATION ION-EXCHANGE RESINS | | |
|---|---|---|
| | | CG-120 |
| AG 50W-X10 | 50W-X10 | IR-122 |
| AG 50W-X12 | 50W-X12 | IR-124 |
| AG 50W-X16 | 50W-X16 | |
| Diamond-Shamrock (DUOLITE) | Permutit Co. (England) | Permutit Co. (U.S.A.) |
| C-20 | ZEOCARB 225 (X4) ZEOCARB 225 | Permutit Q Q-100 |
| C-20 × 10 | | Q-110 |
| C-20 × 2 | | Q-130 |

Weakly acidic cationic ion exchange resins include acrylics such as BIO-REX 70 (Bio-Rad Co.), DUO-LITE (C-3 (Diamond), AMBERLITE (RC-50 and CG 50 (of Rohm and Haas), ZIOCARB 226 (of Permutit-England) and Q-210 (of Permutit Co. of U.S.A.).

Weakly acid chelating cationic ion exchange resins of polystyrene include CHELEX 100 (Bio-Rad) and DOWEX A-1 (Dow).

Mixtures of the aforementioned ion exchange resins may be used in this invention. The presently prefered cationic ion exchange resins include the DOWEX series from the Dow Chemical Company.

The DOWEX 50 and DOWEX 50 W are strong-acid cationic ion exchange resins which are made by the nuclear sulfonation of polymeric styrene-divinyl benzene beads. The DOWEX numbering system, e.g., DOWEX 50 W-X8 is specific to the copolymer composition. The number after the "X" is the measure of the cross-linking. Thus, for example, this resin contains about 8% of divinylbenzene as a cross-linking agent and the remaining about 92% is styrene and other monovinyl monomers.

The presently preferred cationic ion exchange resin is DOWEX 50 W-X8.

Additional detail concerning ion exchange resins is found in the Dow Chemical Company publication, entitled *Dowex: Ion Exchange*, published in Midland, Mich. in 1964 and in *Ion Exchange Properties and Applications* by K. Dorfner, published by Ann Arbor Science Publishers, Inc. in Ann Arbor, Mich. in 1972.

Anionic ion exchange resins are produced by the same companies listed for the cationic ion exchange resins. The company and its brands of resin are listed below:

| ANIONIC ION-EXCHANGE RESINS | | |
|---|---|---|
| Bio-Rad Analytical Grade | Dow Chemical Co. "DOWEX" | Diamond-Shamrock "DUOLITE" |
| AG 1-X1 | 1-X1 | |
| AG 1-X2 | 1-X2 | |
| AG 1-X4 | 1-X4 | A-101D |
| AG 1-X8 | 1-X8 | |
| AG 1-X10 | 1-X10 | |
| AG 21K | 21K | |
| AG 2-X4 | 2-X4 | A-102D |
| AG 2-X8 | 2-X8 | |
| AG 2-X10 | | |
| BIO-REX 9 | | |
| Rohm and Haas Co. "AMBERLITE" | Permutit Co. (England) | Permutit Co. (U.S.A.) |
| | DEACIDITE FF (lightly crosslinked) | S-100 |
| IRA-401 | | |
| IRA-400 and CG-400 IRA-425 | DEACIDITE FF | |
| IRA-402 IRA-410 | | S-200 |
| | | A-580 |

The numerical designations for Bio-Rad resins in the AG catagory are the same as those for "DOWEX" resins, e.g. AG 1-X8 200–400 mesh is the Analytical Grade Bio-Rad resin. AG-1 indicates the type of ionic exchange group, in this case, an anion exchanger; —X indicates the percentage of divinylbenzene crosslinkage, in this case 8% divinylbenzene is incorporated into the polymer beads prior to attaching ionic groups. AG 1 is a strongly basic anion exchange resin composed of quaternary ammonium exchange groups, e.g. —$CH_2N^+(CH_3)_3Cl^-$, attached to a styrene-divinylbenzene polymer lattice. Strongly basic anionic exchangers are obtained by a relatively simple method from the chloromethylation products of styrene-divinylbenzene copolymers by their conversion with tertiary amines.

Mixtures of the cationic ion exchange resins and anion exchange resins are useful to remove both adsorbed anionic and cationic chemical agents from contact lenses. Further, the combination of mixed bed resins having both anionic and cationic portions is commercially available from a number of companies, including Bio-Rad's Analytical Grade, AG 501-X8 and AG 501-X8D; Diamond-Shamrock's DUOLITE GPM-331G; Rohm and Haas' AMBERLITE MB1; Permutit Company's BIO-DEMINERALIT; and INDECALOR BIODEMINERALIT (from England) and M-100 (from the United States).

The concentration of the cationic and/or anionic ion exchange resins used in this invention may range between about 0.1 and 50 percent by weight of the total solution preferably between about 1 and 20 percent by weight. Presently, a most preferred range is between about 5 and 15 percent by weight. Mixtures of the ion exchange resins in the aforementioned ranges are also useful in this invention.

Water

The water used in this invention may in some instances be ordinary tap water. A presently preferred embodiment is the use of deionized or sterile water. In this way no agents harmful to the eye should be present in the solution.

Salt

Saline solutions are also useful in the practice of this invention and require the use of an ophthalmologically acceptable salt, such as, for example, the alkali metal and alkaline earth metal halides. The alkali metals include lithium, sodium, potassium, cesium and rubidium. The alkaline earth metals include beryllium, magnesium, calcium, strontium, and barium. The halogens include fluorine, chlorine, bromine and iodine. Presently prefered salts include sodium chloride, sodium bromide, potassium chloride, potassium bromide and mixtures thereof. The presently most prefered salt is sodium chloride.

The concentration of the salt may vary over a wide range from about 0.01 to 10 percent by weight. A presently preferred range is from about 0.1 to 5 percent by weight. A presently preferred concentration is about 0.9 percent by weight.

Rejuvenation

The process of rejuvenation is carried out by immersing the lens in the composition for a time sufficient to remove the chemical irritants. The rejuvenation may occur at temperatures between about 0° and 90° C. Presently preferred temperatures include about 20° C. and ambient room temperature. The time necessary for rejuvenation will vary depending upon the amount of chemical agents present. The time may vary from a few hours to several days to remove the chemical agents. Normally, a overnight treatment will be sufficient, ranging from about 6–20 hours. Agitation of the solution is usually not required, but will normally accelerate the rejuvenation process. After the rejuvenation process the lenses may be treated with water, a cleaning/or a preserving solution to remove any residual rejuvenation solution.

Preparation

In the preparation of the composition of this invention, i.e., the mixing of the surfactant, ion exchange resin, and optionally water and the salt, may occur in any order. The ion exchange resin(s) used in this invention normally do not dissolve in the aqueous solution. The components may be combined at any temperature between about 0° and 90° C. Presently preferred temperatures include about 20° and ambient room temperature. The composition may be optionally agitated during the preparation.

DESCRIPTION OF SPECIFIC EMBODIMENTS

The following description is given to enable those skilled in this art to more clearly understand and practice the present invention. It should not be considered as a limitation upon the scope of the invention but merely as being illustrative and representative thereof.

PREPARATION 1

Two hydrogel contact lenses, (United States Adoptive Name, Crofilcon A of Syntex Ophthalmics, Inc.) prepared from about 61.5 percent 2,3-dihydroxypropylmethacrylate with methyl methacrylate, crosslinked with ethyleneglycol dimethylacrylate and hydrated to about 38.5 percent water by weight, are contacted with 4 milliliters (ml) of a contact lens sterilizing solution (NORMAL ®, a product of Burton Parsons, Inc., containing chlorhexidine digluconate, CDG). The lenses are treated for about 30 days. A fresh NORMAL solution is used each day. The lenses are shaken dry and the remaining solution is analyzed by ultraviolet spectroscopy to determine the amount of chlorhexidine digluconate present. The difference in CDG concentration is the amount which accumulated in the lens. The results of that study are shown below:

| TOTAL CHLORHEXIDENE DIGLUCONATE ADSORBED IN THE LENS | | |
|---|---|---|
| Day | Lens A ($\mu g$) | Lens B ($\mu g$) |
| 1 | 142 | 166 |
| 2 | 296 | 332 |
| 3 | 432 | 490 |
| 4 | 542 | 618 |
| 5 | 656 | 758 |
| 6 | 758 | 890 |
| 7 | 868 | 1034 |
| 8 | 966 | 1162 |
| 9 | 1056 | 1276 |
| 10 | 1136 | 1382 |
| 11 | 1212 | 1480 |
| 12 | 1290 | 1586 |
| 13 | 1354 | 1690 |
| 14 | 1414 | 1778 |
| 15 | 1468 | 1858 |
| 16 | 1520 | 1934 |
| 17 | 1576 | 2014 |
| 18 | 1622 | 2082 |
| 19 | 1674 | 2146 |
| 20 | 1730 | 2218 |
| 21 | 1768 | 2274 |
| 22 | 1802 | 2326 |
| 23 | 1828 | 2372 |
| 24 | 1862 | 2428 |
| 25 | 1878 | 2470 |
| 26 | 1886 | 2508 |
| 27 | 1898 | 2550 |
| 28 | 1902 | 2580 |
| 29 | — | 2593 |
| 30 | — | 2601 |
| 31 | — | 2607 |
| 32 | — | 2611 |
| 33 | — | 2613 |

Thus, Lens A accumulated 1902 $\mu g$ of chlorhexidine diglucondate, and Lens B accumulated 2613 $\mu g$ during the test period.

PREPARATION 2

As is described in Preparation 1, several lenses are treated with 4-ml of NORMAL ® contact lens solution for several days. Fresh NORMAL solution is used each day and the solution is analyzed for remaining chlorhexidine digluconate (CDG) by ultraviolet spectroscopy. The CDG accumulated in the lenses is the calculated differences in concentration. The details are given in the following list:

| ACCUMULATION OF CHLORHEXIDINE DIGLUCONATE (CDG) IN THE LENS | | | | | | |
|---|---|---|---|---|---|---|
| DAY | C ($\mu g$) | D ($\mu g$) | E ($\mu g$) | F ($\mu g$) | G ($\mu g$) | H ($\mu g$) |
| 1 | 197 | 173 | 160 | 149 | 157 | 240 |
| 2 | 350 | 321 | 318 | 297 | 301 | 410 |
| 3 | 475 | 471 | 415 | 435 | 453 | 579 |
| 4 | 563 | 605 | 499 | 549 | 591 | 755 |
| 5 | 721 | 747 | 583 | 649 | 711 | 900 |
| 6 | 834 | 871 | 660 | 751 | 849 | 1059 |
| 7 | 1002 | 1011 | 741 | 859 | 989 | 1300 |
| 8 | 1131 | 1149 | 816 | 961 | 1113 | 1442 |
| 9 | 1265 | 1261 | 886 | 1047 | 1209 | 1570 |
| 10 | 1391 | 1375 | 956 | 1128 | 1311 | 1685 |
| 11 | 1499 | 1461 | 1025 | 1201 | 1401 | 1795 |
| 12 | 1501 | 1555 | 1096 | 1277 | 1495 | 1890 |
| 13 | 1702 | 1681 | 1171 | 1344 | 1585 | 1991 |
| 14 | 1795 | 1735 | 1253 | 1402 | 1665 | 2099 |
| 15 | 1899 | 1812 | 1325 | 1459 | 1721 | 2178 |
| 16 | 2001 | 1901 | 1399 | 1513 | 1799 | 2287 |
| 17 | 2111 | 1999 | 1460 | 1571 | 1875 | 2359 |
| 18 | 2208 | 2071 | 1521 | 1611 | 1946 | 2423 |
| 19 | 2300 | 2116 | 1540 | 1663 | 2023 | 2499 |
| 20 | 2390 | 2201 | 1561 | 1718 | 2098 | 2551 |
| 21 | 2450 | 2265 | 1591 | 1761 | 2170 | 2659 |
| 22 | 2534 | 2350 | 1623 | 1795 | 2121 | 2746 |
| 23 | 2584 | 2425 | 1649 | 1820 | 2263 | 2840 |
| 24 | 2647 | 2490 | 1661 | 1855 | 2301 | 2845 |
| 25 | 2698 | 2540 | 1669 | 1871 | 2359 | 2901 |
| 26 | 2745 | 2570 | 1679 | 1899 | 2369 | 2946 |
| 27 | 2751 | 2583 | 1690 | 1911 | 2373 | 2958 |
| 28 | 2753 | 2591 | 1700 | 1919 | 2374 | 2964 |
| 29 | 2752 | 2594 | 1706 | 1925 | 2373 | 2966 |

-continued

| | ACCUMULATION OF CHLORHEXIDINE DIGLUCONATE (CDG) IN THE LENS | | | | | |
|---|---|---|---|---|---|---|
| DAY | C ($\mu$g) | D ($\mu$g) | E ($\mu$g) | F ($\mu$g) | G ($\mu$g) | H ($\mu$g) |
| 30 | 2753 | 2596 | 1703 | 1927 | 2375 | 2967 |

Lenses C and D are HEMA [poly(2-hydroxyethyl-methacrylate) 9, while Lenses E, F, G and H are Crofilcon A.

EXAMPLE 1

Lens A, from Preparation 1, containing 1902 $\mu$g of chlorhexidine digluconate, is placed in 10 ml of an isotonic solution containing surfactant, 2% TWEEN 20 solution, containing about 0.9% saline (sodium chloride) for 20 hours. The amount of chlorhexidine digluconate (CDG) released into the solution is measured by treatment of the solution with sodium hypobromite followed by standard colorimetic analysis, and determined to be about 950 $\mu$g. About 50 percent of the chlorhexidine is removed by this process.

EXAMPLE 2

Lens B from Preparation 1, containing 2613 $\mu$g of bound chlorhexidine digluconate, is placed in the composition for 16–20 hours. The composition of this invention was prepared by combining 10 ml of isotonic 2% TWEEN 20 and 0.9% saline (sodium chloride) solution with 1 g of DOWEX 50 W-X8. The residue remaining in the lens is small and is estimated at 250 $\mu$g by immersion of the lens into sodium hydroxide/ethanol solution for about 2 hours. The solution is then treated with sodium hypobromite followed by standard colorimetric analysis. Thus, only about 10 percent of the chlorhexidine (CDG) remains in the lens. It is also noted that DOWEX 50 W-X8 in TWEEN solution may tend to discolor the contact lens slightly. However, if the DOWEX is washed thoroughly with deionized water and then with 2% TWEEN 20 prior to use, this problem is not observed. Also the discoloration of the lens is reversible with repeated washings with 2% TWEEN 20.

The results of Examples 1 and 2 are summarized in the table below:

TABLE

| A COMPARISON OF EXAMPLES 1 AND 2 | | | | | | |
|---|---|---|---|---|---|---|
| Example | Surfactant (%) | Resin (g) | Salt (%) | CDG Before ($\mu$g) | CDG After ($\mu$g) | CDG Remaining (%) |
| 1 | 2 | 0 | 0.9 | 1920 | 950 | 50 |
| 2 | 2 | 1 | 0.9 | 2613 | 250 | 10 |

EXAMPLE 3

Lens C from Preparation 2, containing 2753 $\mu$g of chlorhexidine digluconate, is placed in 10 ml of a surfactant 3% TWEEN 20 solution in 0.9% saline (sodium chloride) for 20 hours. The amount of chlorhexidine digluconate released into the solution, 1453 $\mu$g, is measured as in Example 1. Thus, about 25 percent is removed.

EXAMPLE 4

Lens D from Preparation 2, containing 2596 $\mu$g of chlorhexidine digluconate, is treated with 10 ml of a 3% TWEEN 20 solution in 0.9% saline and 1.0 g of DOWEX 50 W-X8 ion exchange resin for 20 hours. The chlorhexidine digluconate remaining in the lens is 205 $\mu$g (about 8 percent) is measured as in Example 2.

EXAMPLE 5

Lens E from Preparation 2, containing 1703 $\mu$g of chlorhexidine digluconate, is treated with 10 ml of a sterile aqueous solution of 1% TWEEN 20 and 1 g of DOWEX 50 W-X6 for 20 hours. The CDG remaining in the lens is about 170 $\mu$g (about 10 percent) is measured as in Example 2.

EXAMPLE 6

Lens F from Preparation 2 containing 1927 $\mu$g of chlorhexidine digluconate is treated with 10 ml of a saline solution containing 1.0 percent and 2 percent TWEEN 20 and 1.0 g of DOWEX 50 W-X6 for 12 hours. The CDG remaining in the lens is about 250 $\mu$g (about 11 percent) is measured as in Example 2.

EXAMPLE 7

Lens G from Preparation 2, containing 2375 $\mu$g of chlorhexidine digluconate, is treated with 10 ml of a 0.9% saline solution containing 10% TWEEN 40 and 1.0 g of DOWEX 50-W-X4 for 24 hours. The CDG remaining in the lens is about 210 $\mu$g (less than 10 percent) is measured as in Example 2.

EXAMPLE 8

Lens H from Preparation 4, containing 2375 $\mu$g of chlorhexidine digluconate is treated with 10 ml of 0.9% (isotonic) saline solution containing 2.5% of TWEEN 20 and 0.5 g of DOWEX 50 W-X8 for 24 hours. The CDG remaining in the lens is about 249 $\mu$g (about 11 percent) is measured as in Example 2.

EXAMPLES 9–18

Crofilcon A hydrogel contact lenses are treated with NORMAL® solution according to Preparation 1 and the chlorhexidine digluconate (CDG) remaining is measured as in Example 1. Each lens is then placed in a rejuvenating solution for 20 hours to remove the CDG and the loss is determined as in Example 2. The results are given in the following list:

| ACCUMULATION OF CHLORHEXIDINE DIGLUCONATE (CDG) IN LENSES | | | | | |
|---|---|---|---|---|---|
| Ex | CDG Accumulated ($\mu$g./days) | Total Volume (ml.) | Rejuvenating Solution | | |
| | | | Surfactant | Resin | Salt |
| 9 | 1875/27 | 10 | TWEEN 20 (3%) | DOWEX 50 W-X2 (1.0 g) | NaCl (1.0%) |
| 10 | 2953/31 | 10 | TWEEN 21 (2%) | DOWEX 50 W-X4 (0.5 g) | NaCl (0.9%) |
| 11 | 3741/33 | 20 | TWEEN 40 (1%) | DOWEX 50 X-X10 (1.5 g) | NaCl (0.9%) |
| 12 | 2831/30 | 10 | TWEEN 60 (4%) | DOWEX 50 W-X12 (1.0 g) | NaCl (0.9%) |
| 13 | 3381/29 | 10 | TWEEN 61 (2%) | DOWEX 50 W-X8 (0.9 g) | NaCl (0.8%) |
| 14 | 2581/31 | 10 | TWEEN 65 (2%) | DOWEX 50 W-X14 (1.0 g) | NaCl (0.9%) |
| 15 | 2420/26 | 10 | TWEEN 80 (2%) | DOWEX 50 X-X8 (1.0 g) | NaCl (0.9%) |

-continued

ACCUMULATION OF CHLORHEXIDINE DIGLUCONATE (CDG) IN LENSES

| Ex | CDG Accumulated (μg./days) | Total Volume (ml.) | Rejuvenating Solution | | |
|---|---|---|---|---|---|
| | | | Surfactant | Resin | Salt |
| 16 | 2179/29 | 10 | TWEEN 81 (2%) | DOWEX 50 W-X8 (1.0 g) | NaCl (0.9%) |
| 17 | 1875/28 | 10 | TWEEN 20 (2%) | DOWEX 50 X-X8 (1.0 g) | KCl (0.9%) |
| 18 | 2145/30 | 10 | TWEEN 10 (2%) | DOWEX 50 W-X8 (1.0 g) | KCl/NaCl 50/50 (0.9%) |

In Examples 9–18, the solutions are effective to remove large quantities of the preserving agent.

EXAMPLE 19

Crofilcon A hydrogel contact lenses are treated with a BOIL N SOAK solution Burton Parsons, Inc. containing thimerosal according to Preparation 1, and about 5 μg of thimerosal is retained as measured by atomic adsorption spectroscopy. Each lens is then placed in 10 ml of a solution containing 3% TWEEN 20 solution in 0.9% saline and 1.0 g of DOWEX 1-X10 anion ion exchange resin for 20 hours. The thimerosal remaining is about 10 percent of the original concentration as measured by atomic adsorption spectroscopy.

EXAMPLE 20

Crofilcon A hydrogel contact lenses are treated with a FLEXCARE solution from Burton Parsons Co. Inc. as described in Preparation 1. About 2900 μg of chlorhexidine and 2 μg of thimerosal are adsorbed as measured by ultraviolet and atomic adsorption spectroscopy, respectively. The lenses are placed in 20 ml of a solution containing 3% of TWEEN 20, 1 g of DOWEX 50 W-X8, and 1 g of Bio-Rad Analytical Grade AG 1-X4 as a 0.9% saline solution for 20 hours. The remaining chlorhexidene and thimerosal are about 11% and 9% respectively by analysis as described above in this example. After the normal cleaning and disinfecting procedure, these lenses do not create irritation when placed on a rabbit eye for 8-hour periods.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit of this invention without departing from its essential teachings.

What is claimed:

1. An aqueous contact lens solution for removing adsorbed and occluded chemical and biological agents from a contact lens in need of rejuvenation which comprises:
   (a) a nonionic surfactant;
   (b) (i) a cationic ion exchange resin,
       (ii) an anionic ion exchange resin or
       (iii) mixtures of (i) and (ii);
   (c) water; and optionally
   (d) an ophthalmologically suitable salt.

2. The contact lens solution of claim 1 wherein said ion exchange resin is a cationic ion exchange resin.

3. The contact lens solution of claim 2 wherein said suitable salt comprises an alkali metal or alkaline earth metal halide salt.

4. The contact lens solution of claim 3 wherein said alkali metal halide salt is selected from the group consisting of sodium chloride, sodium bromide, potassium chloride, and potassium bromide and mixtures thereof.

5. The contact lens solution of claim 2 wherein said salt is present in an amount of 0.1 to 10 percent by weight.

6. The contact lens solution of claim 5 wherein said salt comprises about 0.9 percent by weight of sodium chloride.

7. The contact lens solution of claim 2 wherein
   (a) said surfactant is present in an amount of about 0.1 to 10 percent by weight;
   (b) said resin is present in an amount of about 0.1 to 50 percent by weight; and P1 (c) water in a quantity sufficient to bring the solution to 100 percent by weight.

8. The contact lens solution of of claim 2 wherein
   (a) said surfactant is a polyoxyethylenated long-chain carboxylic acid ester of sorbitol, sorbitan or sorbide, or mixtures of said esters; and
   (b) said resin is a nuclear sulfonated copolymer comprised of styrene and divinylbenzene.

9. The contact lens solution of claim 2 wherein
   (a) said surfactant is a polyoxyethylenated sorbitan monolaurate containing about twenty moles of ethylene oxide; and
   (b) said resin is a nuclear sulfonated copolymer of about 92 percent styrene and other monovinyl monomers, and about 8 percent divinylbenzene.

10. The contact lens solution of claim 2 wherein
    (a) said surfactant is present in about 0.5 to 5 percent by weight;
    (b) said resin is present in about 1 to 20 percent by weight; and
    (c) in a quantity sufficient to bring the solution to 100 percent by weight.

11. The contact lens solution of claim 2 wherein
    (a) said surfactant is present in about 1 to 3 percent by weight;
    (b) said resin is present in about 5 to 15 percent by weight; and
    (c) water in a quantity sufficient to bring the solution to 100 percent by weight.

12. The contact lens solution of claim 10 wherein
    (a) said surfactant is a polyoxyethylenated sorbitan monolaurate containing about twenty moles of ethylene oxide which is present in about 2 percent by weight; and
    (b) said resin is a nuclear sulfonated copolymer of about 92 percent styrene and other monovinyl monomers and about 8 percent divinyl benzene which is present in an amount of about 10% by weight.

13. The process of rejuvenating a contact lens which comprises contacting a lens in need of rejuvenating with the contact lens solution of claim 2.

14. The process for preparing the contact lens solution of claim 2 which comprises:
    (a) mixing said surfactant with said resin(s) at ambient temperature; and
    (b) diluting said mixture to the desired concentration by the addition of water.

15. The process for preparing the contact lens solution of claim 2 which comprises:
   (a) mixing said surfactant with said resin(s) at ambient temperature; and
   (b) diluting said mixture to the desired final concentration by the addition of a sodium chloride solution.

16. The contact lens solution of claim 1 wherein said ion exchange resin is an anionic ion exchange resin.

17. The contact lens solution of claim 16, wherein said salt is present in an amount of 0.1 to 10 percent by weight.

18. The contact lens solution of claim 17, said salt comprises about 0.9 percent by weight of sodium chloride.

19. The contact lens solution of claim 16 wherein said ophthalmologically suitable salt comprises an alkali metal or alkaline earth metal halide salt.

20. The contact lens solution of claim 19 wherein said alkali metal halide salt is selected from the group consisting of sodium chloride, sodium bromide, potassium chloride, and potassium bromide and mixtures thereof.

21. The contact lens solution of claim 16 wherein
   (a) said surfactant is present in an amount of about 0.1 to 10 percent by weight;
   (b) said resin is present in an amount of about 0.1 to 50 percent by weight; and
   (c) water in a quantity sufficient to bring the solution to 100 percent by weight.

22. The contact lens solution of claim 16 wherein
   (a) said surfactant is a polyoxyethylenated long-chain carboxylic acid ester of sorbitol, sorbitan or, sorbide, or mixtures of said esters; and
   (b) said resin is a trimethylbenzyl ammonium substituted copolymer of styrene and divinylbenzene.

23. The contact lens solution of claim 16 wherein
   (a) said surfactant is a polyoxyethylenated sorbitan monolaurate containing about twenty moles of ethylene oxide; and
   (b) said resin is a trimethylbenzyl ammonium substituted copolymer of about 92 percent styrene and other monovinyl monomers, and about 8 percent divinylbenzene.

24. The contact lens solution of claim 16 wherein
   (a) said surfactant is present in about 0.5 to 5 percent by weight;
   (b) said resin is present in about 1 to 20 percent by weight; and
   (c) water in a quantity sufficient to bring the solution to 100 percent by weight.

25. The contact lens solution of claim 16 wherein
   (a) said surfactant is present in about 1 to 3 percent by weight;
   (b) said resin is present in about 5 to 15 percent by weight; and
   (c) water in a quantity sufficient to bring the solution to 100 percent by weight.

26. The process of rejuvenating a lens which comprises contacting a lens in need of rejuvenating with the contact lens solution of claim 16.

27. The process for preparing the contact lens solution of claim 16 which comprises:
   (a) mixing said surfactant with said resin at ambient temperature; and
   (b) diluting said mixture to the desired final concentration by the addition of water.

28. The process for preparing the contact lens solution of claim 16 which comprises:
   (a) mixing said surfactant with said resin at ambient temperatures; and
   (b) diluting said mixture to the desired final concentration by the addition of a sodium chloride solution.

29. The contact lens solution of claim 1 wherein said ion exchange resin is a mixture of anionic and cationic ion exchange resins.

30. The contact lens solution of claim 29 wherein said ophthalmologically suitable salt comprises an alkali metal or alkaline earth metal halide salt.

31. The contact lens solution of claim 30 wherein said alkali metal halide salt is selected from the group consisting of sodium chloride, sodium bromide, potassium chloride, potassium bromide and mixtures thereof.

32. The contact lens solution of claim 29 wherein said salt is present in an amount of 0.1 to 10 percent by weight.

33. The contact lens solution of claim 32 wherein said salt comprises about 0.9 percent by weight of sodium chloride.

34. The contact lens solution of claim 29 wherein
   (a) said surfactant is present in an amount of about 0.1 to 10 percent by weight;
   (b) said resins are present in an amount of 0.1 to 50 percent by weight; and
   (c) is water in a quantity sufficient to bring the solution to 100 percent by weight.

35. The contact lens solution of claim 29 wherein
   (a) said surfactant is a polyoxyethylenated long-chain carboxylic acid ester of sorbitol, sorbitan, sorbide, or mixtures of said esters;
   (b) said cationic ion exchange resin is a nuclear sulfonated copolymer comprised of styrene and divinylbenzene, and
   (c) said anionic ion exchange resin is a trimethylbenzylammonium substituted copolymer of styrene and divinylbenzene.

36. The contact lens solution of claim 29 wherein
   (a) said surfactant is a polyoxyethylenated sorbitan monolaurate containing about twenty moles of ethylene oxide;
   (b) said cationic resin is a nuclear sulfonated copolymer of about 92 percent styrene and other monovinyl monomers, and about 8 percent divinylbenzene; and
   (c) said anionic ion exchange resin is a trimethyl benzylammonium substituted copolymer of about 92 percent styrene and other monovelent monomers, and about 8 percent divinyl benzene.

37. The process of rejuvenating a lens which comprises contacting a lens in need of rejuvenating with the contact lens solution of claim 29.

38. The contact lens solution of claim 29 wherein
   (a) said surfactant is present in an amount of about 0.5 to 5 percent by weight;
   (b) said resins are present in an amount of about 1 to 20 percent by weight; and
   (c) water in a quantity sufficient to bring the solution to 100 percent by weight.

39. The contact lens solution of claim 29 wherein
   (a) said surfactant is present in an amount of about 1 to 3 percent by weight;
   (b) said resins are present in an amount of about 5 to 15 percent by weight;
   (c) water in a quantity sufficient to bring the solution to 100 percent by weight.

40. The process for preparing the contact lens solution of claim 29 which comprises:
(a) mixing said surfactant with said resins at ambient temperature; and
(b) diluting said mixture to the desired final concentration by the addition of water.

41. The process for preparing the contact lens solution of claim 29 which comprises:
(a) mixing said surfactant with said resins at ambient temperatures; and
(b) diluting said mixture to the desired final concentration by the addition of a sodium chloride solution.

* * * * *